United States Patent [19]

Black

[11] 4,048,177
[45] Sept. 13, 1977

[54] CERTAIN 2-SUBSTITUTED 4-PHENYLQUINOLINE-4-OLS
[75] Inventor: Robin Michael Black, Porton, England
[73] Assignee: John Wyeth & Brother Limited, Maidenhead, England
[21] Appl. No.: 647,278
[22] Filed: Jan. 7, 1976
[30] Foreign Application Priority Data
Jan. 16, 1975 United Kingdom ............... 1932/75
[51] Int. Cl.² ................ C07D 215/22; C07D 215/38
[52] U.S. Cl. .................... 260/288 R; 260/268 BQ; 260/283 SY; 260/287 T; 260/288 CE; 260/289 H; 260/289 K; 424/258
[58] Field of Search .................................. 260/288 R
[56] References Cited
U.S. PATENT DOCUMENTS
3,493,590  2/1970  Plostnieks .................. 260/288 R
3,647,802  3/1972  Carney ....................... 260/288 R OTHER PUBLICATIONS
Carney; Chem. Abst., vol. 74:53559y, (1967).

Primary Examiner—Donald G. Daus
Assistant Examiner—Mary C. Vaughn
Attorney, Agent, or Firm—Arthur E. Wilfond

[57] ABSTRACT

The invention relates to quinoline derivatives of the formula (I)

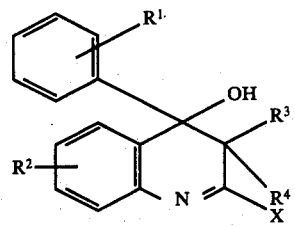

(I)

and the pharmaceutically acceptable acid addition salts of those compounds capable of forming acid addition salts. In formula (I), $R^1$ and $R^2$ which may be the same of different each represent hydrogen, lower alkyl, lower alkoxy, trifluoromethyl or halogen, $R^3$ and $R^4$ which may be the same or different each represent lower alkyl and X represents hydroxy, halogen, hydrazino, or a radical of formula $-NR^5R^6$ where $R^5$ and $R^6$ which may be the same or different each represent hydrogen or lower alkyl or $R^5$ and $R^6$ together with the nitrogen atom to which they are both attached represent a saturated heterocyclic ring containing 5 to 7 ring atoms. The compounds possess hypotensive activity.

7 Claims, No Drawings

CERTAIN 2-SUBSTITUTED 4-PHENYLQUINOLINE-4-OLS

This invention relates to quinoline derivatives. In particular the invention relates to certain novel quinoline derivatives, to methods of preparing the novel derivatives and to pharmaceutical compositions containing them.

The novel quinoline derivatives of the present invention are compounds of the general formula (I)

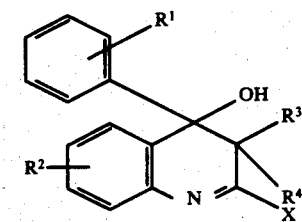

and the pharmaceutically acceptable acid addition salts of those compounds of general formula (I) capable of forming acid addition salts.

In general formula (I) $R^1$ and $R^2$ which may be the same or different each represent hydrogen, lower alkyl, lower alkoxy, trifluoromethyl or halogen, $R^3$ and $R^4$ which may be the same or different each represent lower alkyl and X represents hydroxy, halogen, hydrazino or a radical of formula $-NR^5R^6$ where $R^5$ and $R^6$ which may be the same or different each represent hydrogen or lower alkyl or $R^5$ and $R^6$ together with the nitrogen atom to which they are both attached represent a saturated heterocyclic ring containing 5 to 7 ring atoms.

The term "lower" as used herein means that the radical referred to contains 1 to 6 carbon atoms. Preferably the radical contains 1 to 4 carbon atoms.

Some of the compounds of general formula (I) can exist in tautomeric forms. For example, when X is hydroxy a possible alternative tautomeric structure is

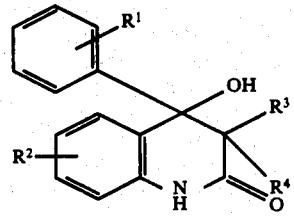

Where in this specification there is used a formula or a name implying one tautomeric form it is to be understood that this formula or name includes any alternative tautomeric form of mixtures of such tautomeric forms.

The following are examples of the groups $R^1$ and $R^2$: hydrogen; lower alkyl (e.g. methyl, ethyl, propyl and butyl); lower alkoxy (e.g. methoxy, ethoxy, propoxy and butoxy); trifluoromethyl and halogen such as fluorine, chlorine and bromine. Preferably both $R^1$ and $R^2$ are hydrogen. $R^3$ and $R^4$ can be the same or different and they represent lower alkyl radicals e.g. methyl, ethyl, propyl and butyl. Preferably $R^3$ and $R^4$ are the same and both represent methyl.

When X is halogen it is preferably bromine or, more especially, chlorine. When X is $-NR^5R^6$, $R^5$ and $R^6$ can be hydrogen or lower alkyl e.g. methyl, ethyl, propyl, butyl. Thus $-NR^5R^6$ can be, for example, amino, methylamino and dimethylamino. When $R^5$ and $R^6$ together with the nitrogen atom to which they are both attached represent a saturated heterocyclic ring, the ring may contain other hetero atoms, especially nitrogen or oxygen. Thus $-NR^5R^6$ may be, for example pyrrolidino, piperidino piperazino or morpholino. The heterocyclic ring may be substituted by additional substituents, for example the heterocyclic ring may be 4-lower alkylpiperazino, 4-arylpiperazine or 4-hydroxyethylpiperazine or a piperidino radical containing an amino group or a substituent -NHCOR where R is for example a substituted or unsubstituted aryl radical (including a heteroaryl radical). Thus, $-NR^5R^6$ can be, for example 4-benzamidopiperidino. Specially preferred compounds are those of general formula (I) in which X is hydroxy, halogen, hydrazino, amino, (lower)alkylamino, di(lower)alkylamino, 4-(lower) alkylpiperazino or 4-benzamidopiperidino, particularly such compounds in which $R^1$ and $R^2$ are both hydrogen.

The compounds of the invention may be prepared by a process in which a 2-aminobenzophenone of general formula (II).

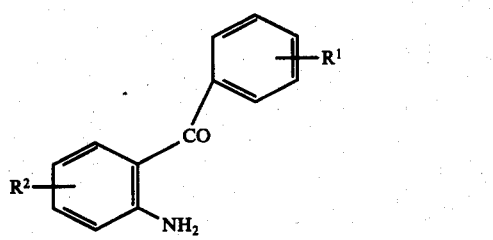

(where R and $R^1$ have the meanings defined above) is reacted with a nitrile of general formula (III)

(where $R^3$ and $R^4$ have the meanings given above) and if desired a resulting compound of general formula (I) wherein X is amino is converted into another compound of general formula (I) by a known method.

The 2-aminobenzophenone of general formula (II) may be reacted with the nitrile of general formula (III) in an inert solvent in presence of a base such as sodium amide, sodium hydride, lithium diisopropylamide or lithium diethylamide. The compound of general formula (I) in which X is amino may be converted into other compounds of general formula (I) by known methods. For example, a compound in which X is amino may be hydrolysed (e.g. with an aqueous alkali) to a compound in which X is hydroxy. Alternatively a compound in which X is amino may be reacted with hydrazine (e.g. anhydrous hydrazine) to give a compound in which X is hydrazino. The compounds in which X is halogen may be prepared by treating the corresponding compound in which X is hydroxy with a hydroxyl/halogen exchange reagent. By "hydroxy/halogen exchange reagent" is meant a reagent capable of displacing the hydroxyl group of an alcohol by a halogen atom. Typical examples are phosphoryl chloride or phosphorus pentachloride. Compounds in which X is -NR⁵R⁶ may be prepared by amination of the corresponding compound in which X is halogen with an amine of formula

  (IV)

This process is particularly applicable to the preparation of compounds in which R⁵ and R⁶ are not both hydrogen; as mentioned above compounds in which R⁵ and R⁶ are both hydrogen may be prepared by reacting a 2-aminobenzophenone of general formula (II) with a nitrile of general formula (III).

In the reaction of compound of the general formula (I) where X is halogen with the amine of general formula (IV) preferably X is chlorine. If it is desired to prepare a compound in which -NR⁵R⁶ is a heterocyclic ring carrying one or more substituents which would interfere with the reaction these substituents may be protected in the amine of general formula (IV) and the protecting groups may be removed subsequently.

If in any of the processes described above the compound of the invention is obtained as an acid addition salt, the free base can be obtained by basifying a solution of the acid addition salt. Conversely if the product of the process is a free base, an acid addition salt, particularly a pharmaceutically acceptable acid addition salt may normally be obtained by dissolving the free base in a suitable organic solvent and treating the solution with an acid, in accordance with conventional procedures for preparing acid addition salts from base compounds. Examples of acid addition salts are those formed from inorganic and organic acids such as sulphuric, hydrochloric, hydrobromic, phosphoric, tartaric, fumaric, maleic, citric, acetic, formic, methanesulphonic and p-toluenesulphonic acids.

The compounds of the invention possess at least one asymmetric carbon atom and hence optical enantiomorphs are possible. The compounds of the invention may be in the form of optical isomers or mixtures of isomers, e.g. racemates. The optical isomers may be prepared from racemic mixtures by the use of standard methods described in the literature.

The compounds of the invention possess hypotensive activity as indicated by a standard pharmacological procedure. In such a procedure the compounds are administered intravenously to normotensive anaesthetised rats and the fall in diastolic blood pressure is measured 15 minutes after administration. Generally the compounds produce a 30 mm. Hg or more fall in blood pressure in this test when administered at a dose of at least 25.6 mg/kg. Many of the compounds are active at lower dosages. For example, 2-hydrazino-3,4-dihydro-3,3-dimethyl-4-phenylquinolin-4-ol exhibited sustained hypotension in the above procedure at a dosage level of 1.6 mg/kg.

Many of the compounds of the present invention are useful as intermediates for preparing other compounds of the present invention e.g. by the processes described above. In addition, compounds in which X is amino may be cyclised to imidazo [1,2-a] quinolines having hypotensive activity as more fully described in my copending currently filed application Ser. No. 647,279 entitled "Imidazo [1,2-a] quinolines" (corresponding to U.K. Application No. 1933/75).

The invention further provides a pharmaceutical composition which comprises a compound of formula (I) or a pharmaceutically acceptable acid addition thereof, in association with a pharmaceutically acceptable carrier. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredients. In tablets the active ingredient is mixed with a carrier having the necessary binding properties in suitable proportions and compacted in the shape and size desired. The powders and tablets preferably contain from 5 to 99, preferably 10–80%, of the active ingredient. Suitable solid carriers are magnesium carbonate, magnesium stearate, talc, sugar, lactose, pectin, dextrin, starch, gelatine, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can be dissolved in a suitable organic solvent, for instance aqueous propylene glycol containing from 10 to 75% of the glycol by weight is generally suitable.

In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical compositions is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these packaged form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form. The daily dose of compound will vary depending upon the route of administration, the particular compound employed and the particular animal involved. The daily dose could be, for example, within the range 0.5 to 20 mg/kg depending upon the method of administration and the specific compound. The following Examples illustrate the invention.

EXAMPLE 1

2-Amino-3,4-dihydro-3,3-dimethyl-4-phenylquinolin-4-ol

Sodium amide (15 g.) was added portionwise to a stirred solution of 2-aminobenzophenone(19.7g., 0.1 mole) and isobutyronitrile (20.7g., 0.3 mole) in dry ether (500 ml.). The mixture was stirred for 1 hour at room temperature and then heated under reflux for 2½ hours. After cooling, the mixture was poured onto ice, extracted with ether and the combined extracts washed and dried (MgSO$_4$). The solvent was removed and the residue crystallised from toluene to give a product (10.76g., m.p. 157° – 160° C). Recrystallisation from toluene gave the pure title compound, 9.17g., m.p. 161° – 163° C. [Found: C. 76.75, H, 6.9, N, 10.5%. $C_{17}H_{18}N_2O$ requires C, 76.65, H, 6.8, N, 10.5%].

A hydrochloride salt crystallised from ethanol/ether, m.p. 277° – 280° C. (dec.). [Found: C, 67.6, H, 6.55, N, 9.05%. $C_{17}H_{18}N_2O$. HCl requires C, 67.45 H,6.3, N, 9.25%].

EXAMPLE 2

3,4-Dihydro-4-hydroxy-3,3-dimethyl-4-phenyl-2(1H)-quinolinone

A solution of 2-amino-3,4-dihydro-3,3-dimethyl-4-phenylquinolin-4-ol (5.32 g., 0.02 mole) in methanol (40 ml.) and 2N aqueous sodium hydroxide (20 ml. ) was heated under reflux for 6 hours. The mixture was poured onto water, extracted with chloroform and the combined extracts washed and dried (MgSO$_4$). After removal of the solvent the residue was crystallised from toluene to give the title compound (4.73g., m.p. 185° – 187° C). [Found: C, 76.25, H, 6.6, N, 5.3% $C_{17}H_{17}NO_2$ requires, 76.4, H, 6.4, N, 5.25%].

EXAMPLE 3

2-Chloro-3,4-dihydro-3,3-dimethyl-4-phenylquinolin-4-ol

Phosphorus pentachloride (7.8g) was added portion wise to a hot stirred solution of 3,4-dihydro-4-hydroxy, 3,3-dimethyl-4-phenyl-2(1H)-quinolinone (8.02 g., 0.03 mole) in dry benzene (250 ml.) and the mixture heated under reflux for one hour. The benzene and phosphoryl chloride were evaporated to yield a white solid which on recrystallisation from toluene gave the title compound (5.8g., m.p. ca 195° – 198° (dec.) [Found: C:71.8, H, 5.9, N, 4.9%, $C_{17}H_{16}ClNO$ requires C, 71.45, H, 5.65, N, 4.9%]

EXAMPLE 4

2-Hydrazino-3,4-dihydro-3,3-dimethyl-4-phenylquinolin-4-ol

2-Amino-3,4-dihydro-3,3-dimethyl-4-phenylquinolin-4-ol (10.0 g., 0.0375 mole) was added to anhydrous hydrazine (34g., 1.06 mole) and the solution refluxed for 5½ hours, cooled, poured on to water, extracted with chloroform, dried and evaporated. Trituration with toluene yielded the title compound as a white solid (9.11g., m.p. 195° – 196° C) [Found: C, 72.5; H, 7.0; N, 14.8% $C_{17}H_{19}N_3O$ requires C, 72.6; H, 6.8; N, 14.9%]

EXAMPLE 5

3,4-Dihydro-3,3-dimethyl-2-methylamino-4-phenyl-quinolin-4-ol

2-Chloro-3,4-dihydro-3,3-dimethyl-4-phenylquinolin-4-ol (1.43g., 0.005 mole) was dissolved in a mixture of a 33% w/v solution of methylamine in ethanol (40 ml.) and pyridine (0.79g.). The solution was stirred for four hours, after which the methylamine and ethanol were evaporated off to leave a residue, which was recrystallised twice from isopropyl alcohol to give the title compound (0.96g., m.p. 192° – 194° C).

The hydrochloride of the title compound was recrystallised from ethanol, m.p. 208° – 210° C [Found: C, 67.8; H, 7.0; N, 8.8% $C_{18}H_{20}N_2O$ HCl requires C, 68.2; H, 6.7; N, 8.8%]

EXAMPLE 6

3,4-Dihydro-3,3-dimethyl-2-dimethylamino-4-phenyl-quinolin-4-ol

2-Chloro-3,4-dihydro-3,3-dimethyl-4-phenylquinolin-4-ol (1.0g., 0.0035 mole) was dissolved in a mixture of a 33% w/v solution of dimethylamine in ethanol (15 ml.) and pyridine (0.6 ml. 0.0075 mole). The solution was stirred for 24 hours, then partially evaporated and allowed to crystallise to give the title compound (0.78g., m.p. 170° – 173° C) [Found: C, 77.4; H, 7.75; N, 9.5% $C_{19}H_{22}N_2O$ requires: C, 77.5; H, 7.5; N, 9.5%].

EXAMPLE 7

3,4-Dihydro-3,3-dimethyl-2-(4-methyl-1-piperazinyl)-4-phenylquinolin-4-ol

2-Chloro-3,4-dihydro-3,3-dimethyl-4-phenylquinolin-4-ol (0.7g., 0.0025 mole) was dissolved in dry dioxan (10 ml.). Triethylamine (0.5g) followed by N-methylpiperazine (1.92g.) were added and the mixture stirred for 4 hours. The mixture was then evaporated down to a white solid residue which was recrystallised from isopropyl alcohol to give the title compound (0.60g., m.p. 268° – 269° C) [Found: C, 75.6; H, 8.1; N, 12.15% $C_{22}H_{27}N_3O$ requires C, 75.6; H, 7.8; N, 12.0%].

EXAMPLE 8

[1-(3,4-Dihydro-4-hydroxy-3,3-dimethyl-4-phenyl-2-quinolinyl)-4-piperidinyl]benzamide To a solution of 2-chloro-3,4-dihydro-3,3-dimethyl-4-phenylquinolin-4-ol (1.0g., 0.0035 mole) in dry dioxan (15 ml.) and triethylamine (1 ml.) was added 4-benzamidopiperidine (0.67 g., 0.0035 mole). After heating at 80° C for 4½ hours, the reaction mixture was cooled, a small amount of solid was filtered off and the filtrate evaporated down to a residue. Trituration with hexane yielded the title compound as the crude free base (m.p. 78° – 81° C). The hydrobromide (1.05g., m.p. 166° – 168° C) was obtained as the monohydrate on crystallisation from isopropyl alcohol. [Found: C, 62.75; H, 6.2; N, 7.3% $C_{29}H_{31}N_3O_2 H_2O$ HBr requires: C, 63.0; H, 6.2; N, 7.6%].

EXAMPLE 9

In a manner analogous to that described in Example 1 isobutyronitrile is reacted with a. 2-amino-5-methoxybenzophenone(Sternbach et al., J. Org.Chem., 1962, 27, 3781)

b. 2-amino-5-methylbenzophenone(Chattaway, J. Chem.Soc., 1904, 589)

c. 2-amino-5-chlorobenzophenone(Chattaway, J. Chem.Soc., 1904, 344)

d. 2-amino-2',5-dichlorobenzophenone(Sternbach et al., J. Org.Chem., 1961, 26, 4488)

and e. 2-amino-5-trifluoromethylbenzophenone(U.K. Patent specification No. 972,973)

to give, respectively, a. 2-amino-3,4-dihydro-3,3-dimethyl-6-methoxy-4-phenylquinolin-4-ol b. 2-amino-3,4-dihydro-3,3,6-trimethyl-4-phenylquinolin-4-ol c. 2-amino-6-chloro-3,4-dihydro-3,3-dimethyl-4-phenylquinolin-4-ol d. 2-amino-6-chloro-4-(o-chlorophenyl)-3,4-dihydro-3,3-dimethylquinolin-4-ol and e. 2-amino-3,4-dihydro-3,3-dimethyl-4-phenyl-6-trifluoromethylquinolin-4-ol.

I claim:

1. A 4-phenylquinolin-4-ol selected from the group consisting of compounds having the formula (I)

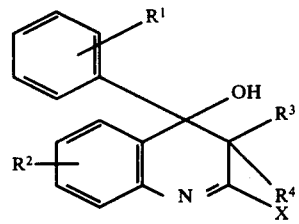

(I)

and the pharmaceutically acceptable acid addition salts thereof, wherein $R^1$ and $R^2$, which may be the same or different, each represent hydrogen, lower alkyl, lower alkoxy, trifluoromethyl or halogen, $R^3$ and $R^4$, which may be the same or different, each represent lower alkyl and X represents hydrazino, amino, (lower)alkylamino, or di(lower)alkylamino, with the proviso that $R^3$ and $R^4$ cannot be groups which give rise to steric hindrance.

2. A compound according to claim 1 wherein $R^1$ and $R^2$ are both hydrogen.

3. A compound according to claim 1 which is 2-amino-3,4-dihydro-3,3-dimethyl-4-phenylquinolin-4-ol or a pharmaceutically acceptable acid addition salt thereof.

4. The compound according to claim 1 which is 2-hydrazino-3,4-dihydro-3,3-dimethyl-4-phenylquinolin-4-ol.

5. A compound according to claim 1 which is 3,4-dihydro-3,3-dimethyl-2-methylamino-4-phenylquinolin-4-ol or a pharmaceutically acceptable acid addition salt thereof.

6. The compound according to claim 1 which is 3,4-dihydro-3,3-dimethyl-2-dimethylamino-4-phenylquinolin-4-ol.

7. A compound according to claim 1, which is 2-hydrazino-3,4-dihydro-3,3-dimethyl-4-phenylquinolin-4-ol or a pharmaceutically acceptable acid addition salt thereof.

* * * * *